United States Patent [19]

Mioduszewski

[11] Patent Number: 5,834,477
[45] Date of Patent: Nov. 10, 1998

[54] OPIATE ANALGESIC FORMULATION WITH IMPROVED SAFETY

[75] Inventor: Robert John Mioduszewski, Bel Air, Md.

[73] Assignee: The United States of America as represented by the Secretary of the Army, Washington, D.C.

[21] Appl. No.: 365,372

[22] Filed: Dec. 27, 1994

Related U.S. Application Data

[63] Continuation of Ser. No. 168,790, Dec. 8, 1993, abandoned.
[51] Int. Cl.⁶ ............................................. A61K 31/14
[52] U.S. Cl. .................. 514/282; 514/811; 514/812; 514/823
[58] Field of Search ..................... 514/823, 811, 514/282, 812

[56] References Cited

U.S. PATENT DOCUMENTS 5,512,578  4/1996  Crain et al. ............................ 514/282

OTHER PUBLICATIONS

Chemical Abstracts AN 1990: 191789, Moore et al, 1990.

Chemical Abstracts AN 1977: 165459, Drummond et al, 1977.

*Primary Examiner*—Keith D. MacMillan
*Attorney, Agent, or Firm*—Ulysses John Biffoni; Edward Goldberg; Michael C. Sachs

[57] ABSTRACT

An opiate analgesic drug formulation which induces minimal respiratory depression is provided which contains a homogeneous mixture of an opiate agonist drug component and an opiate antagonist drug component in an aqueous medium, the opiate agonist component and the opiate antagonist component being present in the mixture in a molar ratio, wherein when the drug formulation is administered to a patient in an amount sufficient for the opiate agonist drug component to induce analgesia in the patient, substantially no respiratory depression is induced in the patient.

11 Claims, No Drawings

OPIATE ANALGESIC FORMULATION WITH IMPROVED SAFETY

This application is a continuation of application Ser. No. 08/168,790, filed Dec. 8, 1993, now abandoned.

GOVERNMENTAL INTEREST

The invention described herein may be manufactured, used, and licensed by or for the United States Government.

FIELD OF THE INVENTION

The present invention relates to analgesic drug formulations and more particularly, to opiate drug formulations which induce analgesia as well as sedation and anesthesia with minimal respiratory depression.

BACKGROUND OF THE INVENTION

The best and most commonly used drugs to relieve pain are opiate narcotics. However, all opiates in clinical use today exhibit some degree of respiratory depression. Heretofore, respiratory problems associated with opiates generally require their administration under conditions of artificial (mechanical) respiratory support with respiration generally being maintained within normal physiological limits by an anesthesiologist.

The need for mechanical respiratory support is an "invasive" procedure which involves intubation of the trachea. The use of such procedures generally requires skilled professionals, sometimes involves trauma to the trachea, and is often associated with discomfort during the recovery period.

Upon termination of surgical procedures requiring an opiate for anesthesia, the analgesic/anesthetic as well as adverse respiratory effects of the opiate are routinely reversed by administering an opiate antagonist. However, the opiate agonist effects may last longer than those of the opiate antagonist, resulting in "renarcotization" and its associated respiratory depression.

Heretofore, the development of opiate drugs to create a drug that causes analgesia without respiratory depression has been an elusive goal. In early opiate research and development work, drug regimens consisting of combinations of pure opiate agonists and other classes of drugs were tested to determine "ideal ratios" that would retain analgesic properties but would not exhibit undesirable effects such as respiratory depression. This early approach, however, did not meet with much success.

While there have been relatively recent developments of opiate drugs, both agonists and antagonists with more selective pharmacologic properties, such developments have not resulted in any significant reduction of respiratory depression associated with the opiate agonists. For example, opiate agonists including synthetic opiate agonists, are used clinically as analgesics, and as adjuncts to anesthesia. However, the use thereof is normally associated with respiratory depression which limits their safety and thus their clinical use without mechanical respiratory support. Although some opiate agonists have been formulated which exhibit limited respiratory depression properties, their potency and thus their utility as analgesics and anesthetics have been limited as well. Currently, opiate antagonists have three main clinical applications: 1) diagnosis of narcotic addiction; 2) prophylactic treatment of narcotic use; and 3) emergency treatment of narcotic overdosage.

Although there have been efforts in the past to develop opiate drug formulations which exhibit reduced respiratory depression, as indicated, the suitability thereof has been limited and the advantages of developing an opiate drug or formulation which exhibited very potent opiate induced sedation, analgesia and anesthesia while the potency thereof for inducing respiratory depression was greatly diminished would be evident.

SUMMARY OF THE INVENTION

It is accordingly an object of the present invention to provide an opiate drug or formulation which allows for very potent induced sedation, analgesia and anesthesia with little or no respiratory depression and thereby precludes, or at least minimizes, the need for mechanical respiratory support, thus permitting procedures requiring analgesia and/or anesthesia to be performed under less rigorous conditions such as, for example, in a field hospital.

It is another object of the present invention to provide a novel opiate drug formulation which effectively dissociates the desired effects of the opiates such as sedation, analgesia and anesthesia from the adverse effects such as respiratory depression of opiates.

It is a further object of the present invention to provide a novel opiate drug formulation containing the mixture of an opiate agonist and an opiate antagonist, preferably in an aqueous and/or saline medium, in proportions wherein the free-base molar ratio of the agonist component to the antagonist component has the potency of an opiate agonist for inducing sedation, analgesia and anesthesia while the potency of the opiate agonist for inducing respiratory depression is greatly diminished.

It is a still further object of the present invention to provide a method for preparing a drug formulation suitable for in vivo administration to a patient wherein a substantially pure opiate agonist is combined with a substantially pure opiate antagonist in an aqueous or saline medium in proportions of opiate agonist to opiate antagonist wherein their free-base molar ratio results in sedation, analgesia and anesthesia with minimal respiratory depression.

In accordance with the present invention there is provided an opiate analgesic drug formulation which induces minimal respiratory depression comprising the mixture of an opiate agonist component and an opiate antagonist component in an aqueous medium, said opiate agonist component and said opiate antagonist component being present in said mixture in a molar ratio, wherein when administered to a patient in an amount sufficient for the opiate agonist drug component to induce analgesia in the patient, substantially no respiratory depression is induced in the patient.

The opiate drug formulation according to the present invention can be used for the in vivo treatment of a patient to promote a very potent induced analgesia as well as sedation and anesthesia while surprisingly and unexpectedly inducing very little or substantially no respiratory depression. Thus, the use of such opiate drug formulation will substantially preclude or minimize the need for mechanical respiratory support and permit procedures requiring analgesia and/or anesthesia to be performed under less rigorous conditions, such as in a field hospital, doctor's office or remote locations.

In another aspect of the invention there is provided a method for preparing an opiate drug formulation suitable for administration to a patient to induce analgesia substantially without the inducement of respiratory depression which comprises forming an aqueous solution of a substantially homogeneous mixture of an opiate agonist drug component suitable to induce analgesia to a patient and an opiate antagonist drug component suitable to serve as a long lasting antagonist, said agonist component being present in said solution in an amount relative to said antagonist component in a free molar ratio wherein administration of said drug formulation in an amount sufficient to induce potent analgesia in a patient will induce minimal respiratory depression.

DETAILED DESCRIPTION OF THE PREFERRED EMBODIMENTS

The novel opiate drug formulation of the present invention comprises a substantially homogeneous mixture of an opiate drug agonist component and an opiate drug antagonist component, preferably in an aqueous medium, wherein the opiate drug formulation is suitable for in vivo administration to a patient such as by intravenous injection or inhalation as an aerosol. The formulation contains an amount of an opiate drug agonist component sufficient to induce potent analgesia as well as anesthesia and sedation and an amount of the antagonist drug component relative to the agonist component, wherein the opiate drug formulation will induce substantially no or minimal respiration depression.

The opiate drug agonist component of the opiate drug formulation of the present invention is an opiate drug agonist which induces sedation, analgesia and anesthesia while also inducing respiratory depression upon in vivo administration to a patient. Suitable for use are substantially pure synthetic opiates in the fentanyl series (e.g., fentanyl, carfentanil and alfentanil) and, preferably, sufentanil oxalate, a synthetic opiate having the formula N-{4-(methoxymethyl)-1-[2-(2-thienyl) ethyl]-4-piperidinyl}-N-phenylpropanamide-oxalate.

The opiate drug antagonist component of the opiate drug formulation of the present invention is a long lasting opiate antagonist which, when coadministered with sufentanil oxalate or other suitable synthetic agonist in a molar ratio to be discussed hereinafter, will block or significantly inhibit respiratory depression with little significant effect on the potency or onset of opiate agonist-induced sedation, analgesia and/or anesthesia. Suitable for use as the opiate antagonist component is Nalmefene HCL having the formula 17-(cyclopropylmethyl)-4,5-epoxy-3,14-dihydroxymorphinan-6-methylene (CAS # 55096-26-9). Also suitable may be pure opiate antagonists such as naloxone and naltrexone.

The opiate drug components are incorporated in the novel opiate drug formulations of the invention in conjunction with an aqueous medium, saline solution etc. in any manner known in the art. A suitable aqueous medium includes sterile water, saline solution (0.9%) or the like which serves as a physiological solvent for intravenously injecting or administrating the drug formulation.

The opiate drug components of the novel opiate drug formulation of the present invention are employed in sufficient concentrations of opiate agonist and opiate antagonist components in the aqueous medium wherein the opiate agonist will induce analgesia, sedation and anesthesia as desired and wherein there is little or no significant effect on the potency or onset of opiate agonist induced sedation, analgesia and anesthesia while the respiratory depression induced by the opiate agonist is blocked or significantly inhibited.

The molar ratio of the opiate agonist component to the opiate antagonist component in the drug formulation is important to achieve the desired combination of potent opiate induced analgesia while respiratory depression is greatly diminished and while the molar ratio to be employed depends on the particular combination of agonist component and antagonist components used, in general, a molar ratio of agonist component to antagonist component in the range of between about 10:1 to about 17:1 would be suitable. For example, in a preferred embodiment of the invention wherein sufentanil oxalate is the opiate agonist component and nalmefene HCL is the opiate antagonist component of the formulation, a molar ratio of about 15:1 of agonist to antagonist is effective for both inducing sedation, analgesia and anesthesia while effectively and substantially inhibiting respiratory depression. The molar ratios of other suitable opiate agonist and opiate antagonist components of the opiate drug formulation to maximize analgesia, sedation and anesthesia while minimizing respiratory depression can be readily determined by those having ordinary skill in the art carrying out routine experimentation.

In preparing the opiate drug formulation of the invention, standard pure opiate agonist and antagonist components as herein described are used. The opiate agonist and antagonist components can be incorporated in an aqueous or saline solution using any method known in the art for preparing drug formulations suitable for intravenous administration to a patient or any other desired method for administration of the drug formulation. Alternatively, separate solutions of each of the opiate drugs can be prepared and then mixed in the desired proportions.

The invention will now be further illustrated by reference to certain specific examples which are provided herein for purposes of illustration only and are not intended to limit the scope therein.

EXAMPLE 1

An opiate drug formulation containing a combination of Sufentanil Oxalate (opiate agonist) and Nalmefene HCl (opiate antagonist) components in a molar ratio of 15:1 is prepared in a saline solution for administration by intravenous infection to a test group of animal patients (Ferrets). A series of tests are performed by administration of the opiate drug formulation on test groups of the test animals (Ferrets) and the pharmacological effects are determined by conventional diagnostic techniques.

The Effective Dose (ED) and Safety Ratio's for drug induced response in 16%, 50% and 84% of Treated Ferrets are reported in Table I, below

TABLE I

| Clinical Sign | Effective Dose (ug/kg of body weight) | | | Safety Ratio[1] |
|---|---|---|---|---|
| | ED16% | ED50% | ED84% | |
| Akinesia | 2.7 (1.8–3.9) | 4.7 (2.1–10.5) | 8.4 (5.7–12.5) | >673 |
| Catalepsy | 2.7 (1.8–3.9) | 4.7 (2.1–10.5) | 8.4 (5.7–12.5) | >673 |
| Loss of Righting | 8.0 (1.1–56.9) | 52.5 (14.0–191.0) | 341.6 (47.9–2432.0) | >60 |
| Anesthesia | 2.5 (0.6–9.7) | 10.0 (3.3–31.5) | 41.8 (10.7–162.1) | >316 |
| Apnea | No evidence of apnea | | | |
| Lethality | No lethalities at any dose tested | | | |

[1]Safety Ratio [(3160 ug/kg/ED50]

For comparison, the pharmacological effects of the administration of Sufentanil Oxalate to a test group of Ferrets by intravenous injection are determined by conventional diagnostic techniques.

The Effective Dosage (ED) and Safety Ratio's for drug induced Responses in 16%, 50% and 84% of treated Ferrets are reported in Table II, below

TABLE II

| Clinical Sign | Effective Dose (ug/kg of body weight) | | | Safety Ratio[1] |
|---|---|---|---|---|
| | ED16% | ED50% | ED84% | |
| Akinesia | 0.9 (0.6–1.3) | 2.0 (0.9–4.5) | 4.6 (3.0–6.9) | 139 |
| Catalepsy | 1.1 (1.3–8.0) | 2.4 (0.8–7.2) | 5.3 (2.5–11.0) | 116 |
| Loss of Righting | 3.4 (1.3–8.0) | 7.8 (2.5–24.5) | 17.8 (7.6–41.9) | 36 |
| Anesthesia | 4.3 (2.6–8.4) | 9.1 (3.5–25.9) | 19.6 (10.9–35.4) | 29 |
| Apnea | 4.3 (2.7–25.5) | 9.1 (3.2–25.5) | 19.2 (10.0–36.7) | 29 |
| Lethality | 34.0 (1.4–780.0) | 285.0 (52.2–1564.5) | 2390.0 (104.7–54794.1) | — |

The effectiveness of a drug formulation containing a combination of an opiate drug agonist and are opiate drug antagonist in a molar ratio of 15:1 for inducing anesthesia without depressing respiratory and other side-effects induced by the use of an opiate drug agonist itself is apparent from the results shown in Tables I and II above.

EXAMPLE II

A series of tests were performed to determine various pharmacological effects of the administration of opiate drug formulations containing mixtures of an opiate drug agonist and an opiate drug antagonist in differing molar ratios. The tests were performed by the intravenous injection administration of test groups of 6 Ferrets each with drug formulations containing a mixture of Sufentanil Oxalate (opiate drug agonists) and Nalmefene HC1 (opiate drug antagonist) in molar ratios of 1:1, 3:1, 10:1, and 17:1, respectively.

The amount of Sufentanil Oxalate used in each drug formulation is equivalent to the lethal dose (LD 84) of such drug.

The Response of the Ferret test animals to the administration of the drug formulation of this example is determined by diagnosis of a variety of clinical signs. The pharmacological effects determined are as reported in Table III.

TABLE III

| Clinical Sign | Percent of Ferrets Responding Molar Ratio of Formulation (Sufentanil:Nalmefene) | | | | |
|---|---|---|---|---|---|
| | 1:1 | 3:1 | 10:1 | 17:1 | Sufentanil(LD84) |
| Akinesia | 84 | 50 | 100 | 100 | 100 |
| Catalepsy | 0 | 0 | 100 | 100 | 100 |
| Loss of Righting | 0 | 0 | 0 | 66 | 100 |
| Anesthesia | 0 | 0 | 66 | 100 | 100 |
| Apnea | 0 | 0 | 0 | 0 | 100 |
| Lethality | 0 | 0 | 0 | 16 | 84 |

The present invention may be embodied in other specific forms without departing from the spirit or essential attributes thereof and accordingly reference should be made to the appended claims rather than to the foregoing specification as indicating the scope of the invention.

What is claimed is:

1. An opiate analgesic drug formulation which induces minimal respiratory depression comprising a substantially homogeneous mixture of an opiate agonist drug component and an opiate antagonist drug component in an aqueous medium, said opiate agonist component and said opiate antagonist component being present in said mixture in a molar ratio, between about 10:1 and about 17:1, such that analgesia is maintained but substantially no respiratory depression is induced in the patient.

2. The opiate analgesic drug formulation as claimed in claim 1, wherein said opiate agonist drug component is sufentanil oxalate.

3. The opiate analgesic drug formulation as claimed in claim 1, wherein said opiate antagonist drug component is Nalmefene HCL.

4. The opiate analgesic drug formulation as claimed in claim 3, wherein said opiate agonist drug component is sufentanil oxalate and the relative proportion of said opiate agonist drug component to said opiate antagonist drug component in said drug formulation is in a molar ratio of about 15:1.

5. A method for preparing an opiate drug formulation suitable for administration to a patient for inducing analgesia substantially without the inducement of respiratory depression which comprises forming an aqueous solution of a substantially homogeneous mixture of an opiate agonist drug component suitable for inducing analgesia in a patient and an opiate antagonist drug component suitable to serve as a long lasting antagonist, said agonist/antagonist components being an a free molar ratio between about 10:1 and about 17:1, wherein administration of said drug formulation in an amount sufficient to induce potent analgesia in a patient will induce minimal respiratory depression.

6. The method for preparing an opiate drug formulation as claimed in claim 5, wherein a saline solution is used to prepare said aqueous solution.

7. An opiate analgesic drug formulation which when administered induces analgesia substantially without inducement of respiratory depression, said formulation being produced by forming an aqueous solution of a substantially homogeneous mixture of an opiate agonist drug component and an opiate antagonist drug component, wherein said agonist component is present in said solution relative to said antagonist component in a molar ratio between about 10:1 and 17:1, so that administration of said drug formulation in an amount sufficient to induce potent analgesia in a patient will induce minimal respiratory depression.

8. The drug formulation of claim 7, wherein a saline solution is used to prepare said aqueous solution.

9. The drug formulation of claim 7, wherein said opiate agonist drug component is sufentanil oxalate.

10. The drug formulation of claim 7, wherein said opiate antagonist drug component is Nalmefene HC1.

11. The drug formulation of claim 7, wherein said opiate agonist drug component is sufentanil oxalate and the relative proportion of said opiate agonist drug component to said opiate antagonist drug component in said drug formulation is in a molar ratio of about 15:1.

* * * * *